(12) United States Patent  
Leslie-Martin et al.

(10) Patent No.: US 8,864,493 B2  
(45) Date of Patent: Oct. 21, 2014

(54) DENTAL APPLIANCE, DENTAL APPLIANCE ADHESIVE AND RELATED METHODS AND USES

(71) Applicant: Symdent, Inc., Longmont, CO (US)

(72) Inventors: Laurel Rae Leslie-Martin, Longmont, CO (US); Neil Brian Cramer, Boulder, CO (US); Charles Couch, Pueblo, CO (US); Michael Cole, Longmont, CO (US)

(73) Assignee: Symdent, Inc., Longmont, CO (US)

( * ) Notice: Subject to any disclaimer, the term of this patent is extended or adjusted under 35 U.S.C. 154(b) by 0 days.

(21) Appl. No.: 13/674,714

(22) Filed: Nov. 12, 2012

(65) Prior Publication Data

US 2013/0078594 A1    Mar. 28, 2013

Related U.S. Application Data

(63) Continuation-in-part of application No. PCT/US2011/036528, filed on May 13, 2011.

(60) Provisional application No. 61/334,496, filed on May 13, 2010.

(51) Int. Cl.
| | |
|---|---|
| *A61C 7/08* | (2006.01) |
| *A61K 6/00* | (2006.01) |
| *A61L 24/06* | (2006.01) |
| *A61C 13/15* | (2006.01) |

(52) U.S. Cl.  
CPC .............. *A61C 7/08* (2013.01); *A61K 6/0023* (2013.01); *A61L 24/06* (2013.01); *A61C 19/003* (2013.01)  
USPC ............................................................ 433/6

(58) Field of Classification Search  
USPC .............................................................. 433/6  
See application file for complete search history.

(56) References Cited

U.S. PATENT DOCUMENTS

| | | | |
|---|---|---|---|
| 5,362,769 | A | 11/1994 | Waller et al. |
| 5,575,645 | A | 11/1996 | Jacobs et al. |
| 5,976,893 | A | 11/1999 | Chishti et al. |
| 6,554,611 | B2 | 4/2003 | Chishti et al. |
| 6,572,372 | B1 | 6/2003 | Phan et al. |

(Continued)

FOREIGN PATENT DOCUMENTS

WO        2011143520 A2    11/2011

OTHER PUBLICATIONS

Loctite Medical Adhesives Brochure, The Adhesive Sourcebook 2010, pp. 161-172.*  
Invisalign. Ask the Expert Call. Feb. 18, 2007. 76 pages.

*Primary Examiner* — Ralph Lewis  
(74) *Attorney, Agent, or Firm* — Marsh Fischmann & Breyfogle LLP

(57) ABSTRACT

A dental appliance has an auxiliary feature bonded to a polymeric surface of a shell body with a compartment for receiving teeth. The auxiliary feature is bonded with a light-curable acrylic adhesive comprising acrylate base material and photoinitiator. Auxiliary features include colored layers and, decals, reinforcing features and auxiliary dental devices. A light-curable acrylic adhesive may include a thiol monomer and/or a pigment. A dental appliance may have a shell body with a bonding surface adapted for attachment of an auxiliary feature, such as prepared by a pretreatment to mar the surface of to impregnate the surface with a reactive adhesion promoter.

32 Claims, 4 Drawing Sheets

(56) References Cited

U.S. PATENT DOCUMENTS

| | | |
|---|---|---|
| 6,722,880 B2 | 4/2004 | Chishti et al. |
| 7,121,825 B2 | 10/2006 | Chishti et al. |
| 7,553,157 B2 * | 6/2009 | Abolfathi et al. ............. 433/6 |
| 2002/0081546 A1 * | 6/2002 | Tricca et al. ............. 433/6 |
| 2002/0192617 A1 | 12/2002 | Phan et al. |
| 2003/0008259 A1 * | 1/2003 | Kuo et al. ............. 433/6 |
| 2003/0190575 A1 | 10/2003 | Hilliard |
| 2003/0190576 A1 | 10/2003 | Phan et al. |
| 2007/0207440 A1 | 9/2007 | Chen et al. |
| 2007/0231765 A1 * | 10/2007 | Phan et al. ............. 433/6 |
| 2008/0003541 A1 * | 1/2008 | Leslie-Martin ............. 433/215 |
| 2008/0274335 A1 | 11/2008 | Bowman et al. |
| 2009/0270528 A1 | 10/2009 | Bowman et al. |
| 2010/0129762 A1 | 5/2010 | Mason et al. |

\* cited by examiner

DENTAL APPLIANCE, DENTAL APPLIANCE ADHESIVE AND RELATED METHODS AND USES

CROSS-REFERENCE TO RELATED APPLICATIONS

This application is a continuation-in-part of International Patent Application No. PCT/US2011/036528 filed on May 13, 2011 entitled "DENTAL APPLIANCE, DENTAL APPLIANCE ADHESIVE AND RELATED METHODS AND USES", which claims priority to U.S. Provisional Application Ser. No. 61/334,496 filed on May 13, 2010 entitled "DENTAL APPLIANCE, DENTAL APPLIANCE ADHESIVE AND RELATED METHODS AND USES". Each and every part of International Patent Application No. PCT/US2011/036528 and U.S. Provisional Application Ser. No. 61/334,496 is incorporated herein by reference as if set forth herein in full.

FIELD OF THE INVENTION

The invention relates to dental appliances, adhesives for use with dental appliances, and related methods and uses.

BACKGROUND OF THE INVENTION

An aligner-type orthodontic appliance has a polymeric shell that generally covers most or all of the teeth when worn. The appliances are often highly transparent and clear, to an extent that it may be difficult to detect that the appliance is being worn. Some or all of the tooth-receiving interior of the appliance is configured so that when worn, the walls of the appliance apply a force to an adjacent tooth or teeth that over time urges the tooth or teeth in a particular way to effect a movement of the tooth or teeth as part of an orthodontic treatment to reposition the teeth. The urging force is provided by the energy stored in a spring-like deformation of the appliance walls as the appliance is forced onto the teeth and into the position when the appliance is worn. It is the slow dissipation of this stored energy the triggers the underlying processes of tooth movement.

Aligner therapy often involves a series of progressive appliances to progressively reposition teeth. Each aligner may be used for a relatively short period of time, on the order of perhaps a few to several weeks. A new aligner is then applied that urges further movement of the teeth. In this sense, the series of appliances may be considered to be progressively biased. Additional aligners are used until the teeth have been urged to move a desired final positioning.

Such aligner-type appliances may be made by a variety of techniques, which may be performed in a commercial laboratory or on-site at an orthodontist office. One technique is by thermoforming over a model corresponding to a configuration for treatment of the patient's teeth, using a thermoforming machine such as the Biostar Thermoformer or other similar dental thermoforming device. Such thermoforming may be performed at commercial laboratories or on-site at orthodontists' offices. Appliances made by such thermoforming devices are sometimes referred to as "suck-down" appliances, reflecting the use of a vacuum to help form a heated sheet of polymeric material to the pattern of the model. A variety of polymeric materials have been used to make thermoformed appliances. Various blends of such polymers have been used to achieve different combinations of mechanical and optical properties.

One commercially available fabrication service for alignment-type appliances is known as the Invisalign® program. Invisalign® products are not made by a suck-down technique. The Invisalign® aligner fabrication process is technologically sophisticated and uses digitization of impressions and pictures of teeth and 3D computer imaging.

Aligner-type appliances are widely used in a variety of orthodontic situations, and there is a significant need for versatility in such appliances to meet a wide variety of treatment considerations.

For some orthodontic treatments involving the use of aligner-type shells, it is desirable to attach orthodontic components to the outside of the shell. One bonding adhesive that has been proposed for that purpose is the light-activated ClearLoc™ adhesive, which has been reported in a Material Safety Data Sheet to contain 50-55 percent polyurethane oligomer, 26-39 percent high boiling point (meth)acrylate, 15-26 percent aliphatic amide, 1-5 percent photoinitiator and 0.01 to 1 percent organic dye. Appliances with orthodontic components attached using the ClearLoc™ adhesive have had some limited success, but attached components do not uniformly display a level of bond strength or durability that may be desired in many of the wide variety of orthodontic situations, or other dental situations.

Although highly clear, transparent appliance shells are often desirable to "hide" the presence of the appliance, in some instances it would be desirable to have appliances that are not transparent, or not entirely transparent. For example, especially with younger orthodontic patients, adding colorful decoration to the appliance may make the appliance more desirable as personal ornamentation and may promote better compliance with an orthodontic treatment program. It has been proposed, for example, to esthetically enhance appliances by attaching decorative items to the appliance, for example dental decals, using the ClearLoc™ adhesive. However, decals are not ideal for customizing decoration to the particular patient and, as already noted, the ClearLoc™ adhesive has not satisfied bond strength and durability needs for a variety of situations.

SUMMARY OF THE INVENTION

A first aspect of the invention is provided by a dental appliance positionable to be worn within the oral cavity to receive and cover at least a portion of a dentition of a subject, typically a human subject. The dental appliance comprises a shell body comprised of polymeric material and having a compartment within the shell body configured to receive at least a portion of one or more tooth of the dentition when the appliance is worn. The shell body has an interior surface on the inside of the compartment and an exterior surface opposite the interior surface, generally on the outside of the appliance opposite the compartment. An auxiliary feature is bonded to the polymeric material of the body with a cured product of a light-curable acrylic adhesive. The light-curable acrylic adhesive comprises acrylate base material comprising polymerizable acrylic functionality and a photoinitiator.

A number of feature refinements and additional features are applicable to the first aspect of the invention. These feature refinements and additional features may be used individually or in any combination. As such, each of the following features may be, but are not required to be, used with any other feature or combination of the first aspect.

The acrylic functionality may include one or more than one acrylic chemistry-based functional group. By "acrylic functionality" it is meant at least one functional moiety with a polymerizable carbon-carbon double bond of acrylic chemistry. The acrylic functionality may, for example, be or include one or more than one member from a group consisting of an acrylate group, a methacrylate group, an acrylamide group and a methacrylamide group. In one preferred implementation, the acrylic functionality comprises an acrylate group.

The acrylate base material may preferably comprise multiple acrylic functionality. By "multiple acrylic functionality" it is meant that the acrylate base material contains a compound with more than one (i.e., at least two) functional moieties each containing a polymerizable carbon-carbon double bond of acrylic chemistry. Multiple acrylic functionality may also be referred to herein as "polyacrylic functionality". The multiple acrylic functionality of a compound may include only multiple occurrences on the compound of the same acrylic functionality (the same functional group) or may include one or more occurrences of each of two or more different acrylic functionalities. For example, the multiple acrylic functionality may be provided by two or more than two occurrences of an acrylate group on a compound, or two or more than two occurrences of a methacrylate group on a compound, or two or more than two occurrences of an acrylamide group on a compound or two or more than two occurrences of a methacrylamide group on a compound. As another example, the multiple acrylic functionality may be provided by one or more than one occurrences on a compound of each of at least two different members selected from the group consisting of an acrylate group, a methacrylate group, an acrylamide group and a methacrylamide group. In one preferred embodiment, the multiple acrylic functionality is provided by at least two acrylate groups on a compound of the acrylate base material. A compound with at least two acrylate groups may be referred to as a "polyacrylate". A compound with just two acrylate groups may be referred to as a "diacrylate", a compound with just three acrylate groups may be referred to as a "triacrylate", etc.

The acrylate base material may comprise, or may consist essentially of, urethane acrylate, comprising polyurethane repeating units and the polymerizable acrylic functionality. The urethane acrylate may include one or more multiple different urethane acrylate components. A urethane acrylate component may have only a few or many of the polyurethane repeating units. For example, a urethane acrylate component for the urethane acrylate base material may be a "mer" material (e.g., dimer, trimer, etc.), an oligomer, a prepolymer, or a polymer. In one preferred implementation, the urethane acrylate comprises a urethane acrylate oligomer. By "urethane acrylate" it is meant a component having both urethane and acrylic functionality. The urethane functionality may be provided by the polyurethane repeating units. The acrylic functionality will often be in terminal groups at one or both ends of urethane chains. Specific examples of acrylate base materials include aromatic urethane acrylate, polyester diacrylate, ethoxylated (3) trimethylolpropane triacrylate and tricyclodecane dimethanol diacrylate. In one preferred embodiment, the acrylate base material may comprise, or may consist essentially of, one, or optionally more than one, polyacrylate. Examples of some polyacrylate materials for use as an acrylate base material component are ethoxylated (3) trimethylolpropane triacrylate, ethoxylated (3) bisphenol A diacrylate, tricyclodecane dimethanol diacrylate and urethane acrylates with multiple acrylate functionality.

The light-curable acrylic adhesive may also include an unsaturated adhesion promoter copolymerizable with the acrylate base material, and preferably copolymerizable with acrylic functionality, which may be one or more than one of the acrylic functionalities when the acrylate base material comprises multiple acrylic functionality. The unsaturated adhesion promoter may be any material copolymerizable with the acrylic functionality. The unsaturated adhesion promoter may comprise one or more than one adhesion-promoting moiety, and may include one or multiple occurrences of any such adhesion-promoting moiety. In one preferred embodiment, the unsaturated adhesion promoter comprises an adhesion-promoting moiety comprising a carbonyl group. Such an adhesion-promoting moiety may, for example, include one or more of a carboxyl group, an ester linkage and an amide group. The unsaturated adhesion promoter may include one or multiple different unsaturated adhesion-promoting compounds, wherein each such unsaturated adhesion-promoting compound comprises a polymerizable carbon-carbon double bond and an adhesion-promoting moiety comprising a carbonyl group. The unsaturated adhesion promoter, may, for example, include one or more than one compound selected from the group consisting of unsaturated carboxylic acids, unsaturated esters and unsaturated amides. Some specific examples of some unsaturated adhesion-promoting compounds for the unsaturated adhesion promoter include acrylic acid, methacrylic acid, an acrylate ester, a methacrylate ester, a diacrylate ester, an acrylic ester, acrylamide, methacrylamide, N,N-dimethylacrylamide (also referred to simply as dimethylacrylamide), and modified acrylamides. Other examples of some unsaturated adhesion-promoting compounds for the unsaturated adhesion promoter include ethoxylated (3) trimethylolpropane triacrylate, ethoxylated (3) bisphenol A diacrylate, tricyclodecane dimethanol diacrylate, 1,4-butanediol diacrylate, polyester diacrylates and 2-phenoxyethyl acrylate. In one preferred embodiment the unsaturated adhesion promoter comprises multiple different unsaturated adhesion-promoting compounds, with at least one such compound comprising a carbonyl group linked to nitrogen (for example, characteristic of an amide) and with at least one other such compound comprising a carbonyl group linked to oxygen (for example characteristic of an ester or carboxylic acid). As will be appreciated from the above description, some components may be used either as, or as part of, an acrylate base material or an unsaturated adhesion promoter. Some examples are ethoxylated (3) trimethylolpropane triacrylate, ethoxylated (3) bisphenol A diacrylate and tricyclodecane dimethanol diacrylate.

In one embodiment, the unsaturated adhesion promoter may be substantially free of acrylamide functionality. By "substantially free" of a substance, it is meant that there is none of the substance present or an insignificant amount of the substance. In another embodiment, the light-curable adhesive may be substantially free of acrylamide functionality. In some cases, the presence of acrylamide functionality may impart an undesirable high degree of hydrophilicity to the light-curable acrylic adhesive or to the cured product of the light-curable acrylic adhesive.

The photoinitiator may be any photoinitiator used in light-curable acrylic adhesive formulations. Examples of some photoinitiators include diphenyl (2,4,6-trimethylbenzoyl)-phosphine oxide (Darocur TPO, Ciba), phosphine oxide, phenyl bis (2,4,6-trimethyl benzoyl) (Irgacure 819, Ciba), bis(eta 5-2,5-cyclopentadien-1-yl) Bis[2,6-difluoro-3-(1H-pyrrol-1-yl)phenyl]titanium (Irgacure 784, Ciba).

The light-curable acrylic adhesive may comprise any relative amounts of the acrylate base material and photoinitiator, and optionally the unsaturated adhesion promoter when present, that on curing provide a bond sufficient for securely holding the auxiliary feature to the polymeric material of the shell body. The light-curable acrylic adhesive will often comprise acrylate base material at a concentration within a range having a lower limit of 10 weight percent, preferably 15 weight percent or even 20 weight percent and an upper limit of 70 weight percent, preferably 60 weight percent or even 50 weight percent. When the light-curable acrylic adhesive includes an unsaturated adhesion promoter, the light-curable acrylic adhesive will often comprise unsaturated adhesion promoter at a concentration within a range having a lower limit of 15 weight percent, preferably 20 weight percent or even 25 weight percent and an upper limit of 80 weight percent, preferably 70 weight percent or even 60 weight percent. The light-curable acrylic adhesive will often comprise photoinitiator at a concentration within a range having a lower limit of 0.1 weight percent, preferably 0.5 weight percent or even 1 weight percent and an upper limit of 10 weight percent, preferably 6 weight percent or even 4 weight percent. When only one component is present in the light-curable acrylic adhesive that, as described herein, could serve either as an acrylate base material or an unsaturated adhesion promoter, that component will in that particular composition necessarily serve as an acrylate base material in the adhesive composition. If a second component is present in the light-curable acrylic adhesive that, as described herein, could serve either as an acrylate base material or an unsaturated adhesion promoter, that second component may serve as an unsaturated adhesion promoter in the adhesive composition. Often, the acrylate base material will be present in the composition of the light-curable acrylic adhesive at a higher concentration by weight than the unsaturated adhesion promoter. Often, the unsaturated adhesion promoter will have a lower molecular weight than the acrylate base material, which may be conducive to the unsaturated adhesion promoter more preferentially wetting the substrate to which the light-curable adhesive may be applied. When the light-curable acrylic adhesive does not include unsaturated adhesion promoter, the acrylate base material will often be present in the light-curable acrylic adhesive at a concentration in a range having a lower limit of 60 weight percent or 80 weight percent and having an upper limit of 95 weight or 99.9 weight percent. When the light-curable acrylic adhesive includes both acrylate base material and unsaturated adhesion promoter, the combined concentration of the acrylate base material and the unsaturated adhesion promoter will often be in a range having a lower limit of 60 weight percent or 80 weight percent and having an upper limit of 95 weight percent or 99 weight percent. The acrylate base material may be comprised in the light-curable acrylic adhesive of multiple different acrylate base material components and the unsaturated adhesion promoter, when present, may likewise be comprised of multiple different unsaturated adhesion promoter components. In one embodiment, the acrylate base material may be comprised of only a single acrylate base material component.

Optionally, the light-curable acrylic adhesive may comprise one or multiple other components other than acrylate base material, unsaturated adhesion promoter, and photoinitiator, provided that such other component or components are not incompatible with the desired bonding function to be provided by the light-curable acrylic adhesive. Some examples of other possible components include processing aids, rheology modifiers, adhesion-promoting components other than the unsaturated adhesion promoter, oligomeric or polymeric materials (e.g., for structural purposes) other than the acrylate base material, fumed silica and glass fillers.

In one preferred implementation, the light-curable acrylic adhesive may comprise a thiol monomer, which is copolymerizable with the acrylate base material, e.g., with at least one or all of the acrylic functionality of the acrylate base material. When unsaturated adhesion promoter is present, the thiol monomer may be copolymerizable also with the unsaturated adhesion promoter. Many light-curable acrylic adhesive compositions tend to form a tacky surface layer on exposed surfaces of the adhesive composition exposed to oxygen in the air during curing. This tacky layer may be removed following curing, such as by wiping it off with a damp cloth. However, addition of the thiol monomer may reduce or eliminate the development of such tacky surfaces, and may reduce or eliminate the need to remove such tacky layers following curing. The thiol monomer may be any one or more than one compound containing a thiol group (—SH) and that are copolymerizable with one or both of the acrylic functionality of the acrylate material and the unsaturated adhesion promoter. A thiol monomer may advantageously comprise at least one polythiol compound, containing two or more thiol groups. Some specific examples for the thiol monomer include trimethylolpropane tri-3-mercaptopropionate, pentaerythritol tetra-3-mercaptopropionate, glycol di-3-mercaptopropionate, trimethylolpropane trimercaptoacetate, pentaerythritol tetramercaptoacetate, and 1,6-hexanedithiol, available from Evans Chemetics. These examples are all polythiol compounds. When present in the light-curable acrylic adhesive, the thiol monomer may be in any suitable amount, and will often be present in the light-curable acrylic adhesive at a concentration within a range having a lower limit of 1 weight percent, 2 weight percent, 3 weight percent, 5 weight percent or 8 weight percent and having an upper limit of 40 weight percent, 35 weight percent, 30 weight percent, 25 weight percent or 20 weight percent. The use of thiol monomer may be particularly advantageous when the cured product of the light-curable acrylic adhesive in the dental appliance will have significant exposed surfaces, such as when the bonded product provides a colored layer to impart coloration to all or a portion of the shell body. When the light-curable acrylic adhesive includes thiol monomer, the combined weight percentage of the acrylate base material and thiol monomer, and also the unsaturated adhesion promoter when present, may be in a range having a lower limit of 60 weight percent or 80 weight percent and an upper limit of 99 weight percent or 99.9 weight percent. The thiol monomer of the light-curable acrylic adhesive may be comprised of multiple different thiol monomer components.

The light-curable acrylic adhesive is light-curable in that the composition cures in response to at least some applied radiation within the infrared, visible light or ultraviolet range, and preferably in the visible light range. The photoinitiator may be selected to promote curing in response to the desired range or ranges of radiation.

The dental appliance may be of a type generally referred to as a shell-type appliance (which includes the aligner-type appliances) that have a shell body generally of crescent shape that generally corresponds with the arched shape of a dental arch. When worn, the shell covers all or a portion of the dentition. The dental appliance may be an active appliance or a passive appliance. By passive appliance, it is meant that the dental appliance serves a primarily cosmetic function, such as to provide a decorative appearance, which may be for example artistically fanciful or camouflage, to fully or partially conceal from view a portion of the dentition, for example one or more of the teeth or a one or more edentulous sites of the subject. By an active appliance, it is meant that the dental appliance serves a dental function, which may be an orthodontic function, such as for example to assist in the repositioning of teeth as part of an orthodontic treatment. As an example, the dental appliance may be an aligner-type appliance with the shell body configured to apply force to teeth to cause movement of the teeth. For example, the shell body may be configured so that when worn, force is applied to the teeth through the interior surface of the shell body, to cause movement of teeth received in the compartment. The polymeric material of the shell body may be any polymeric material used for preparing such dental appliances. Examples of some materials for the polymeric material include polymeric compositions based on or containing ethylene vinyl acetate, polycarbonates, low-density polyethylene, polypropylene, sheet acrylic, polyethylene terephthalate, poly butyrate, polyvinyl chloride or polyurethane. The polymeric material may comprise a mixture of polymers and may comprise other components. In one implementation, the polymeric material of the shell body is transparent, such that the subject's dentition would be visible through the wall of the shell body absent the application of a colored layer to cover and impart coloration to a surface of the shell body. The transparent polymeric material may be clear, i.e., substantially without color.

The auxiliary feature may be any useful feature that may be bonded to the polymeric material of the shell body using the light-curable acrylic adhesive, or more specifically with the cured product resulting from curing the light-curable acrylic adhesive. The auxiliary feature may be a layer of the cured product of the light-curable acrylic adhesive that is bonded to the shell body, or a component or components contained within such cured product. The layer of the cured product itself, and the components contained therein, may be all that is bonded to the shell body through the bond formed by the cured product of the light-curable acrylic adhesive. Alternatively, the auxiliary feature may be a separate device that is held in relation to the shell body through a bond of the cured product of the light-curable acrylic adhesive with both the shell body and the separate device. A significant advantage of the dental appliance is that the light-curable acrylic adhesive may be used to bond with a variety of different materials of construction from which such device may be partially or entirely made. For example, the light-curable acrylic adhesive may be used to bond with either metallic surfaces or polymeric surfaces of a device. The auxiliary feature may be purely ornamental or may have a functional aspect in relation to a dental or orthodontic treatment. Examples of some purely ornamental auxiliary features include decorative decals or ornamental objects (e.g., jewelry items). In the case of a decal or ornamental object, the cured product of the light-curable adhesive may be clear so as not to visually interfere with the pattern of the decal or the ornamentality of the ornamental object.

In one implementation, the auxiliary feature comprises coloration provided by a colored layer of the cured product of the light-curable acrylic adhesive bonded to the polymeric material of the shell body. The colored layer may cover at least a portion of one or both of the interior surface and exterior surface of the shell body. Coloration is imparted by pigment included in the composition of the light-curable acrylic adhesive. The pigment may be any one or more pigment components included in the light-curable acrylic adhesive that provide or react to provide a desired color effect to the cured product. The pigment is added solely for coloration, and is distinguished from other components in the light-curable acrylic adhesive that are present for mechanical or other purposes, such as for mechanical stability, strength, adhesion, rheology, curing, etc. The pigment will typically serve no function in the light-curably acrylic adhesive other than to impart desired coloration to the resulting cured product. In some compositions for the light-curable acrylic adhesive, fillers, initiators or other components may incidentally impart color to the composition. For example, LOCTITE®3971™ and 3972™ adhesives are clear, whereas LOCTITE® 3554™ Indigo™, 3555™ Indigo™, and 3556™ Indigo™ adhesives are naturally a yellowish color. It should be appreciated that such natural coloration may affect the types and amount of pigments added to obtain a desired color effect in a colored layer. By "colored layer" of the cured product, it is meant that the layer of the cured product has a coloration feature imparted by pigment for a decorative or camouflage purpose, and not a layer which may simply have some incidental coloration aspect due to the natural color of residue of the active components of the light-curable acrylic adhesive. In one implementation, absent inclusion of the pigment, the cured product of the light-curable acrylic adhesive is substantially clear, while in other implementations, absent inclusion of the pigment the cured product exhibits some natural color from other components. When included in the light-curable acrylic adhesive, the pigment will often be in a concentration range having a lower limit of 0.1 weight percent, preferably, 0.3 weight percent or even 0.5 weight percent and having an upper limit of 10 weight percent, preferably 8 weight percent or even 6 weight percent.

In one implementation, the shell body has a facial side that is disposed on a facial side of the dentition of the subject when the appliance is worn and the shell body has a lingual side disposed on a lingual side of the dentition when the appliance is worn, and the colored layer imparts coloration to at least a portion of the facial side of the shell body that is visible when the body is viewed from the facial side. This implementation is advantageous for example, to provide a decorative appearance, such as purely for ornamentation or to camouflage of all or a portion of the dentition that is covered by the shell body. For example, the coloration may be selectively applied to cover and camouflage only certain portions of the dentition, such as to selectively cover and camouflage an edentulous site or sites or one or more than one discolored teeth. As another example, the entire facial side of the shell body could by colored to portray teeth of desired brightness or whiteness corresponding to a natural tooth color. The colored layer may impart desired tooth color to the facial side of the shell body that covers all or a portion of the dentition. Alternatively, the colored layer may impart a purely decorative appearance, such as coloration designed to obviously not be a tooth color, for example, including a color such as red, blue, yellow, green, orange, purple, black, etc. Such decorative coloration may for example, be one solid color or a pattern. A pattern may be any pattern that may be painted or otherwise applied to the desired surface of the shell body. To obtain the pattern, more than one differently pigmented compositions of light-curable acrylic adhesive may be applied to different portions of the shell body, as an artist might use a palette of different colors to paint a picture. The colored layer may, therefore, impart a different color to different portions of the shell body. Also, particular coloration may involve applying an additional layer with color on top of one or more prior-applied layers with color, either before or after curing the prior-applied layer or layers.

In addition to, or instead of, imparting coloration to a facial side of the shell body, the colored layer could also impart coloration to all or a portion of an occlusal side of the shell body and/or to the lingual side of the shell body. An occlusal side of the shell body is a surface of the shell body that faces the opposite dentition when worn. For example, an occlusal surface of the lower dentition would face generally toward the upper dentition, and an occlusal surface of the upper dentition would face generally toward the lower dentition.

The colored layer may be applied to and cover at least a portion of the exterior surface of the shell body. However, in one preferred implementation, the colored layer may be applied to and cover at least a portion of the interior surface of the compartment that receives the dentition, and with the shell body being transparent at least adjacent to the colored layer, so that the coloration provided by the colored layer is visible through the transparent wall of the shell body. In this way, the colored layer may be disposed, for example, on an interior surface on a facial side of the compartment of the shell body, so that the colored layer is within the compartment and protected from the external environment to which the exterior surface of the shell body is subjected, but with the colored layer being visible from the facial side through the transparent wall of the shell body when the shell body is viewed from the facial side.

In one implementation, the light-curable acrylic adhesive used to make the colored layer may include a fragrance, which may impart a fragrant scent, or odor, to the cured product that forms the colored layer. The fragrance may be any material that imparts a desired scent to the light-curable acrylic adhesive and/or the final colored layer after curing. The fragrance may help to mask otherwise unpleasant odors that would be emitted from the light-curable acrylic adhesive or the final cured product, or may simply impart a pleasant odor without providing a masking function. When included in a light-curable acrylic adhesive, the fragrance may be in any desired amount, and is often in a concentration range of 0.1 weight percent to 6 weight percent. Similar to the situation with pigment, a fragrance component will ordinarily serve no purpose other than to impart the scent.

The auxiliary feature may be an auxiliary dental device bonded to the external surface of the shell body, which may for example be on a facial side or a lingual side of the shell body. The auxiliary dental device may be any device serving a dental purpose during a dental treatment. The auxiliary dental device may be for use in an orthodontic treatment, or may be for use in a non-orthodontic dental treatment. The cured product of the light-curable acrylic adhesive may bond to either a metallic surface or to a polymeric surface of the auxiliary dental device. For example, the auxiliary dental device may be or include a stainless steel feature that is bonded to the polymeric material of the shell body through the cured product of the light-curable acrylic adhesive. As another example, the dental appliance may be made from or include a feature made from a polymeric material that is bonded directly to the polymeric material of the shell body through the cured product of the light-curable acrylic adhesive. For example, the polymeric material of the auxiliary dental device may be of a type listed as examples for the polymeric material of the shell body, or may be of a different type of polymeric material. In one implementation, the auxiliary dental device comprises a polycarbonate material of construction that is bonded to the shell body through the cured product of the light-curable acrylic adhesive. In one implementation, the auxiliary dental device may be a custom device shaped from a light-curable composite material. Examples of some auxiliary dental devices include eyelets, hooks, buttons, spurs and wires.

In one implementation, the auxiliary feature comprises a stiffening reinforcement feature bonded to at least a portion of the exterior surface of the shell body to locally stiffen a portion of the shell body for increased resistance to deformation of a wall of the shell body, thereby increasing the force exerted by that wall to one or more teeth received in the compartment adjacent the wall when the appliance is worn. In this implementation, the stiffening reinforcement feature permits different portions of the shell body to be selectively stiffened to provide a greater force for assisting in the repositioning of a tooth or teeth received in the compartment at those selected portions of the shell body. The stiffening reinforcement feature may comprise a reinforcing volume of the cured product of the light-curable acrylic adhesive bonded to a selected portion of an exterior surface of the shell body corresponding to a location within the component where one or more teeth is to be subjected to a locally enhanced force. In one variation, the shell body may have a dimple, or other relief pattern, with a protrusion on an interior surface in the compartment and a corresponding recession on an exterior surface opposite the protrusion, and with a reinforcing volume of the cured product of the light-curable acrylic adhesive disposed at least in part in the recess, and preferably to at least substantially fill the recess. Such a dimple or other relief pattern may be made in a shell body, for example, by a device similar to a pair of pliers that may be used to grasp the shell body and emboss the dimple or other relief pattern into the wall of the shell body. The stiffening reinforcement feature may comprise a stiffening reinforcement member. A stiffening reinforcement member may be made, for example, from a polymeric composition such as those examples noted for the polymeric material of the shell body.

The dental appliance may comprise multiple auxiliary features bonded to polymeric material of the shell body, and which may be the same, similar or different designs, to serve the same, similar or different functions.

A second aspect of the invention is provided by a method for making a dental appliance positionable to be worn within the oral cavity to receive and cover at least a portion of the dentition of a subject. The method comprises applying a light-curable acrylic adhesive to a surface of polymeric material of a shell body comprising an interior compartment to receive at least a portion of one or more tooth of the dentition when the appliance is worn and curing the light-curable acrylic adhesive. The curing is performed in the absence of any portion of a tooth received in the interior compartment. The curing is not performed as part of an operation to fit or attach the dental appliance to the teeth, and the dental appliance is not positioned for wearing during the curing. During the curing, the applied light-curable acrylic adhesive is subjected to a light source sufficient to cause the light-curable acrylic adhesive to cure to form a cured product bonded to the surface of the polymer material of the shell body.

A number of feature refinements and additional features are applicable to the second aspect of the invention. These feature refinements and additional features may be used individually or in any combination. As such, each of the following features may be, but are not required to be, used with any other feature or combination of the first aspect.

The dental appliance made according to the second aspect may be a dental apparatus as described with respect to the first aspect of the invention, and all of the discussion concerning features of the dental apparatus of the first aspect of the invention apply equally to the dental apparatus of the second aspect of the invention, including without limitation with respect to the shell body and the polymeric material of the shell body, the auxiliary feature, the light-curable acrylic adhesive and the cured product of the light-curable acrylic adhesive, and necessary and optional components for inclusion in the light-curable acrylic adhesive, including with respect to acrylate base material, unsaturated adhesion promoter, photoinitiator, pigment, fragrance and thiol monomer.

The light-curable acrylic adhesive for the second aspect may be or have any features as described for the light-curable acrylic adhesive described with respect to the first aspect of the invention or the fourth aspect of the invention (discussed below).

In one implementation of the method of the second aspect of the invention, during the curing an auxiliary feature is bonded to the polymeric material of the shell body. The auxiliary feature may be as described with respect to the first aspect of the invention, for example a colored layer in the form of a cured product of the light-curable acrylic adhesive containing pigment, or a decal, or a stiffening reinforcement feature or an auxiliary dental device. In one implementation when the auxiliary feature is a colored layer, the colored layer comprises different colors in different portions of the colored layer covering different portions of the shell body. For example, to one portion of the interior surface of a compartment of a shell body may be applied one formulation of the light-curable acrylic adhesive with pigment to provide one distinct color when cured, and one or more other formulations of the light-curable acrylic adhesive may be applied to one or more other portions of the interior surface, with the one or more other formulations including different pigments to provide other, different colors when cured. The colored layer over different portions of the shell body may, therefore, have different colors, and may form for example a geometric, artistic, or other colored pattern.

In one implementation of the method of the second aspect of the invention, the method may comprise, prior to applying the light-curable adhesive, forming a dimple or some other relief pattern with a recess on an exterior surface of the shell body and a corresponding protrusion on an opposing interior surface of the shell body. The applying may include applying light-curable acrylic adhesive to fill at least a portion of the recess, and preferably to fill substantially all of the recess, to provide a reinforcing volume of the cured product following the curing.

In one implementation, the method of the second aspect may comprise, prior to applying a light-curable acrylic adhesive to a surface of the polymeric material of the shell, pretreating at least the surface to which the light-curable acrylic adhesive is to be applied. The pretreating may comprise contacting the surface to be pretreated with pretreatment composition that alters the surface to promote enhanced bonding with the cured product of the light-curable acrylic adhesive after the light-curable acrylic adhesive is applied to the surface and cured. The pretreatment composition may comprise, or may consist essentially of, adhesion promoter, which adhesion promoter may be or comprised of one or multiple adhesion promoter components.

In one implementation such a pretreating may comprise marring the surface. A marred surface may have more surface texture, or surface irregularities, to provide more surface area for bonding and to provide better surface topography for mechanical interconnection for good bonding. Marring the surface may be facilitated by an adhesion promoter that is a solvent for at least a portion of the polymeric material of the shell body at the surface that is being pretreated. The adhesion promoter may be nonreactive, in that the polymeric adhesion promoter does not chemically react with components of the light-curable acrylic adhesive to be applied to the surface after the pretreating. When the adhesion promoter is nonreactive, it may be convenient to remove most or substantially all of the adhesion promoter from the surface following the pretreating and prior to applying the light-curable adhesion promoter. Removal of nonreactive adhesion promoter may be facilitated by using volatile components that will tend to largely vaporize prior to applying the light-curable acrylic adhesive and/or through mechanical aids such as being wiped off. Examples of some components for nonreactive adhesion promoter include acetone, ethyl acetate, dimethylsulfoxide, N-methylpryrrolidone, dimethyl formamide, acetonitrile, tetrahydrofuran and toluene, which each may be used alone, in any combination with each other or in combination with other components.

In one implementation pretreating may comprise impregnating the surface with a reactive adhesion promoter. By reactive adhesion promoter it is meant an adhesion promoter with one or more component that is chemically reactive with one or more components of the light-curable acrylic adhesive, such as when the light-curable acrylic adhesive is cured. The reactive adhesion promoter may be copolymerizable with acrylate base material and/or unsaturated adhesion promoter of the light-curable acrylic adhesive. In that regard, the reactive adhesion promoter may include vinyl or acrylic functionality, which may participate in polymerization reactions during curing of the light-curable acrylic adhesive. Components for reactive adhesion promoter for the pretreating may be any of the materials described for use for unsaturated adhesion promoter in the light-curable acrylic adhesive described with the first aspect of the invention. Some specific example components for reactive adhesion promoter include divinyl benzene, vinyl acetate and tetrahydrofuryl acrylate. Examples of some more preferred components for reactive adhesion promoter include vinyl acrylate, cyanoacrylates and N-vinylpyrrolidone. Examples of some even more preferred components for reactive adhesion promoter include dimethylacrylamide and N-methyl-N-vinylacetamide. Any of these example components may be used alone or in any combination with each other or with other components of the pretreatment composition. The pretreatment composition may include both nonreative adhesion promoter and reactive adhesion promoter.

By "impregnating" the surface with reactive adhesion promoter, it is meant having residual reactive adhesion promoter on the surface and preferably also having reactive adhesion promoter penetrating below the surface into the shell body. The penetration may be enhanced by an effective marring of the surface to create greater surface topography. Also, more soluble components of the polymeric material of the shell body may be leached to some extent during the pretreating, leaving behind near-surface voids that may be penetrated by the reactive adhesion promoter. In one preferred implementation, the pretreating comprises both marring the surface and impregnating the surface with reactive adhesion promoter. The reactive adhesion promoter may itself be a solvent for at least a portion of the polymeric material of the shell body, or the pretreatment composition may include a separate solvent, such as for example a nonreactive adhesion promoter.

During the pretreating, the pretreatment composition may be applied in any appropriate manner to contact the surface to be treated, for example by wiping it on to the surface with a cloth or other applicator. The pretreating may comprise wiping the pretreatment composition on the surface, for example to promote dissolving polymeric material of the shell body into the pretreatment composition and/or to help force reactive adhesion promoter to fill surface topography and to promote penetration of reactive adhesion promoter into the near-surface region of the shell body.

A third aspect of the invention is provided by a method of orthodontic treatment for repositioning one or more tooth of a patient, comprising positioning a dental appliance within the oral cavity of the patient to cover at least a portion of the dentition of the patient with one or more tooth received within the compartment and biased by the structure of the body to cause movement of at least one tooth received in the compartment.

A number of feature refinements and additional features are applicable to the third aspect of the invention. These feature refinements and additional features may be used individually or in any combination. As such, each of the following features may be, but are not required to be, used with any other feature or combination of the first aspect.

The dental appliance may be a dental appliance as described with respect to the first or second aspects of the invention and the discussions with respect to the dental appliance, and features thereof, described with respect to the first and second aspects of the invention apply equally with respect to the third aspect of the invention.

In one implementation of the method of the third aspect of the invention, the orthodontic treatment comprises successively fitting a series of multiple different ones of such a dental appliance to the dentition to cause different movements of one or more of the teeth. The compartment of the shell body of each of the dental appliances in the series is differently configured to effect a different tooth movement. For example each successive dental appliance may effect a further tooth movement relative to the movement effected by the prior dental appliance in the series. The series of dental appliances may include a series of aligners for progressively moving the teeth to a desired final configuration. Such a series of dental appliances will often include three or more different ones of the dental appliances. In one refinement of this implementation, different auxiliary features may be bonded to the shell body of at least to different ones of the dental appliances in the series, or even different auxiliary features for every one of the different dental appliances in the series. In one refinement of this implementation, differently colored layers (e.g., containing different colors and/or different colored patterns) may be bonded to the shell body of different ones of the dental appliances in the series, and in a preferred variation of this refinement, at least three different ones of the dental appliances in the series have colored layers that are differently colored from each other. Differently colored layers on successive dental appliances may have an advantage of maintaining interest by orthodontic patients and increasing compliance with a treatment program.

A significant advantage of the method of the third aspect of the invention is that the particular colors or pattern applied to the shell body may be individually tailored to the individual subject.

A fourth aspect of the invention is provided by a light-curable acrylic adhesive useful for forming a colored layer bonded to and covering a polymeric surface of a dental appliance. The light-curable acrylic adhesive is as described above with respect to the first through third aspects of the invention, with the light-curable acrylic adhesive comprising one or both of (i) pigment that imparts a desired coloration for a colored layer of the cured product of curing the light-curable acrylic adhesive and (ii) thiol monomer copolymerizable with one or both of acrylic functionality of acrylate base material and unsaturated adhesion promoter.

A number of feature refinements and additional features are applicable to the fourth aspect of the invention. These feature refinements and additional features may be used individually or in any combination. As such, each of the following features may be, but are not required to be, used with any other feature or combination of the first aspect.

The light-curable acrylic adhesive of the fourth aspect of the invention may include any of the features described with respect to any of the first through third aspects of the invention. In one preferred implementation of the fourth aspect of the invention, the light-curable acrylic adhesive may comprise both pigment and thiol monomer. In another preferred implementation of the fourth aspect, the light-curable acrylic adhesive may comprise a fragrance. In another preferred implementation of the fourth aspect of the invention, a kit includes multiple separately contained volumes of the light-curable acrylic adhesive, with the different volumes of light-curable acrylic adhesive formulated with different pigments, to impart different colors to the colored layer resulting from curing different ones of the volumes of the light-curable acrylic adhesive. The kit is useful to permit the dental professional and patient to select and apply a colored layer with a desired color or a desired pattern with multiple colors. In one implementation, the multiple separately-contained volumes of light-curable acrylic adhesive are packaged together in a single package, for example in a single box or case or wrapped together within cellophane, paper or other wrapping material. The separately-contained volumes may each be contained, for example, in separately-sealed bottles, vials, tubes, etc.

A fifth aspect of the invention is provided by a dental appliance positionable to be worn within the oral cavity to receive and cover at least a portion of a dentition of a subject, typically a human subject. The dental appliance comprises a shell body comprised of polymeric material and having a compartment within the shell body configured to receive at least a portion of one or more tooth of the dentition when the appliance is worn. The shell body has an interior surface on the inside of the compartment and an exterior surface opposite the interior surface, generally on the outside of the appliance opposite the compartment. The shell body has a bonding surface that comprises one or both of the following features: (i) the bonding surface is marred and (ii) the bonding surface is impregnated with a reactive adhesion promoter. By the bonding surface being "impregnated" with reactive adhesion promoter, it is meant that the bonding surface has residual reactive adhesion promoter on the surface and preferably also has reactive adhesion promoter penetrating below the surface into the shell body, in a manner as described previously with the second aspect of the invention. By the bonding surface being "marred" it is meant that the bonding surface has been altered to provide surface topography characteristics conducive to good bonding with a light-curable acrylic adhesive, such as described as resulting from the marring that may occur during the pretreating described with the second aspect of the invention.

A number of feature refinements and additional features are applicable to the fifth aspect of the invention. These feature refinements and additional features may be used individually or in any combination. As such, each of the following features may be, but are not required to be, used with any other feature or combination of the fifth aspect.

The dental appliance of the fifth aspect of the invention may be or have any of the features described for the first aspect of the invention, but the dental appliance of the first aspect of the invention need not include the auxiliary feature bonded to the polymeric material of the shell body with a cured product of a light-curable adhesive. The dental appliance of the fifth aspect may, for example, be a dental appliance as described for the first aspect of the invention before that dental appliance has had the auxiliary feature bonded to it, but which has been subjected to the pretreating described with the second aspect of the invention, prior to applying a light-curable acrylic adhesive to the surface of the polymeric material of the shell body. The bonding surface of the dental appliance of the fifth aspect may be adapted for bonding an auxiliary feature to the shell body with a light-curable acrylic adhesive, such as a surface that has been subjected to pretreating as described with the second aspect of the invention, to mar and/or to impregnate reactive adhesion promoter at the location of the bonding surface. The dental appliance of the fifth aspect may have no auxiliary features bonded to the shell body, or may have one or more than one auxiliary features already bonded to the shell body on which the bonding surface has been prepared for attaching an additional auxiliary feature to the shell body. The reactive adhesion promoter may be according to the discussion provided with the second aspect of the invention concerning the reactive adhesion promoter in relation to the second aspect of the invention. In one implementation, the reactive adhesion promoter for the fifth aspect of the invention is capable of copolymerizing with at least one component of the light-curable acrylic adhesive, as discussed with pretreating with the second aspect of the invention. The light-curable acrylic adhesive may be as described with the respect to any of the first through fourth aspects of the invention.

Additional aspects of the invention are provided by uses of the dental appliance of the first aspect of the invention, the light-curable acrylic adhesive of the fourth aspect of the invention and the dental appliance of the fifth aspect of the invention. The dental appliance of the first aspect of the invention may be used, for example, for a dental treatment, which may be an orthodontic treatment, for example to treat for poor alignment or malocclusion of teeth. The light-curable acrylic adhesive of the fourth aspect of the invention may be used, for example, to form a colored layer or to provide a reinforcement feature, or to bond an auxiliary dental device to a dental appliance (e.g., to the dental appliance of the fifth aspect of the invention), or to bond some other auxiliary dental feature to a surface of polymeric material of a shell body of a dental appliance. For example, the dental appliance of the fifth aspect of the invention may be used for preparing a dental appliance with an auxiliary feature bonded to a shell body, such as to prepare a dental appliance of the first aspect of the invention.

DETAILED DESCRIPTION

Figure 1A:
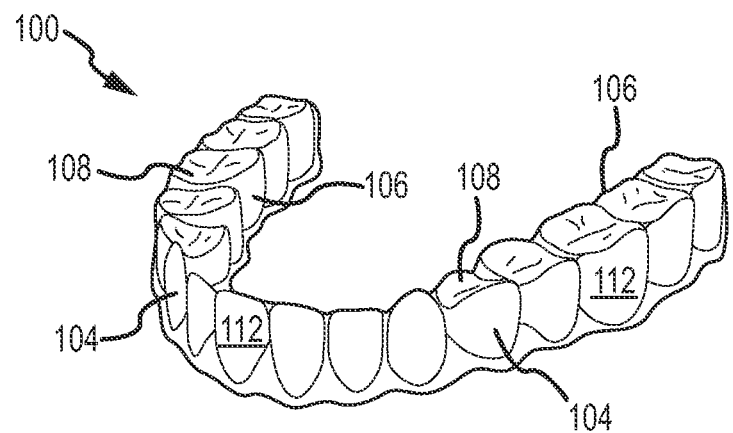
FIGS. 1A and 1B show perspective views of a dental appliance shell body, viewed from different orientations.
Figure 1B:
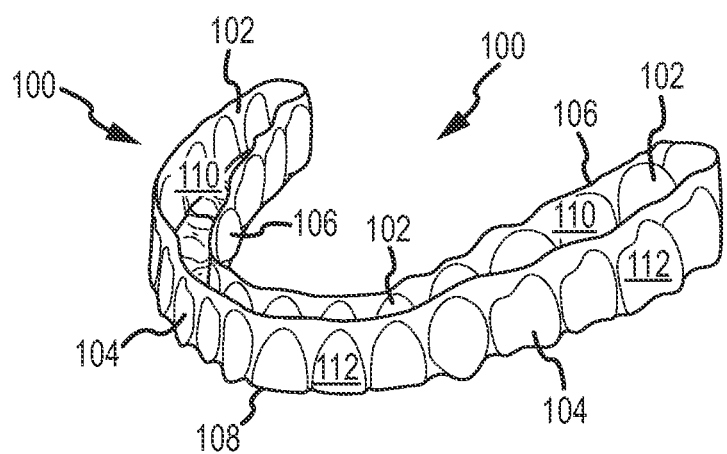

FIGS. 1A and 1B show a shell body 100, such as a type often used for an aligner. FIGS. 1A and 1B present views of the shell body 100 from different orientations to better illustrate the features of the shell body 100. The shell body 100 includes transparent walls that form an interior compartment 102, in which the dentition of a subject is received when the shell body 100 positioned in the mouth to be worn to cover the dentition. The shell body 100 has a generally crescent shape that generally corresponds with the shape of a dental arch. The compartment 102 is configured generally to conform with the shape of the teeth of the subject's dentition that is to be covered by the shell body when worn. The shell body 100 has a facial side 104, which is the side on the side of the shell body 100 that is disposed on the facial side of the subject's dentition when the shell body 100 is worn. When worn, all or portions of the facial side 104 may be clearly visible when the subject's mouth is open. The shell body 100 has a lingual side 106, which is on the side of the shell body 100 that is disposed on the lingual side of the subject's dentition when the shell body 100 is worn. The shell body 100 also includes an occlusal side 108, which generally corresponds with the side of the shell body 100 that covers the top biting surfaces of the teeth when the shell body is worn. The shell body 100 includes an interior surfaces 110, which are the surfaces of the compartment adjacent the dentition when the shell body is worn. The interior surfaces 110 are generally configured to conform to the surfaces of the teeth of the dentition to be received in the compartment of the shell body 100. The shell body 100 also includes exterior surfaces 112, opposite the interior surfaces 110, which are exposed in the subject's mouth when the shell body 100 is worn. As will be appreciated, there are interior surfaces 110 and exterior surfaces 112 on each of the facial side, the lingual side and the occlusal side of the shell body 100.

Figure 2:
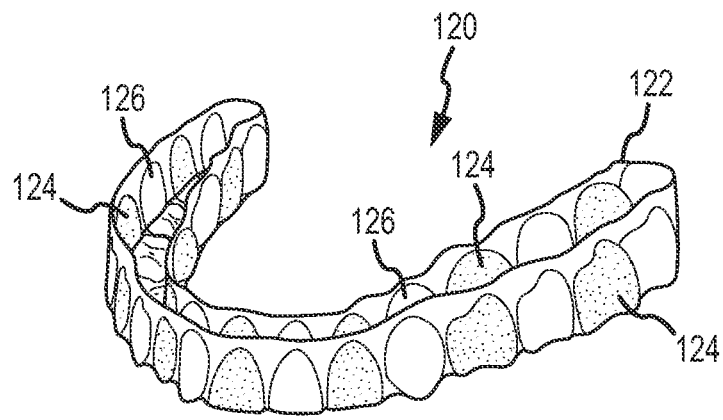
FIG. 2 shows a perspective view of a dental appliance with a colored layer bonded to a shell body.

Referring now to FIG. 2, a dental appliance 120 is shown. The dental appliance 120 includes a shell body 122, generally of a type as described with respect to FIGS. 1A and 1B. Bonded to the shell body 122 are occurrences of a colored layer 124 that selectively imparts coloration to different portions of the shell body 122. As shown in FIG. 2, the colored layer 124 is disposed over selected portions of the interior surface 126 of the interior compartment of the shell body 122. The walls of the shell body are transparent and, therefore, the colored layer 124 is visible when viewing the exterior surfaces of the shell body 122. For example, when the shell body 122 is viewed from the facial side, occurrences of the colored layer 124 disposed on the facial side of the compartment are visible through the transparent wall of the shell body between the exterior and interior surfaces. The different occurrences of the colored layer 124 may be the same or different colors, or each occurrence of the colored layer 124 may be a pattern design. The colored layer 124 is in the form of a layer of cured product from curing a light-curable acrylic adhesive of the invention comprising pigment to impart the desired coloration to the colored layer 124.

Figure 3:
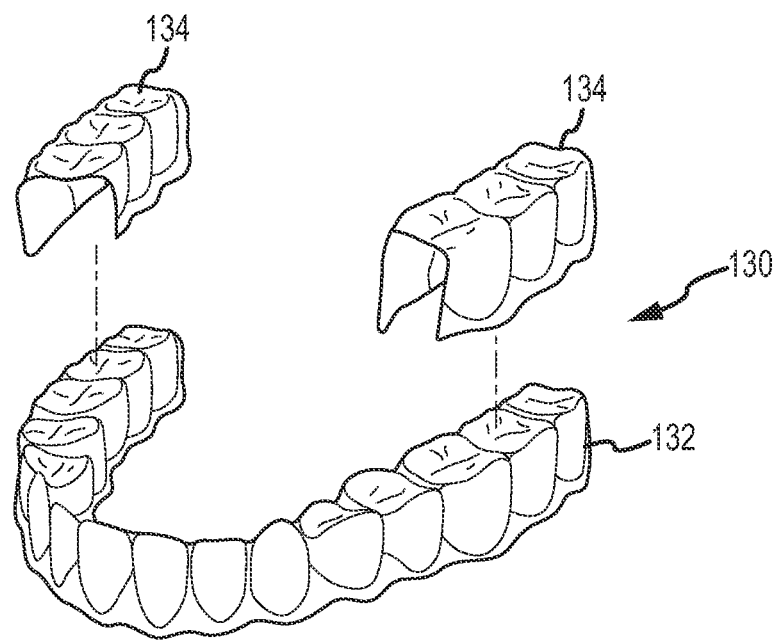
FIG. 3 shows a perspective exploded view of a dental appliance with reinforcement members.

Referring now to FIG. 3, a dental appliance 130 is shown in an exploded view. The dental appliance 130 includes a shell body 132 and two reinforcement members 134. The reinforcement members 134 fit over and conform to the shape of selected portions of the shell body 132. The reinforcement members 134 are bonded to the exterior surface of the shell body 132 by a cured product of a light-curable acrylic adhesive according to the invention. The reinforcement members 134 add additional wall thickness to supplement the wall thickness of the shell body 132. The added wall thickness selectively provides additional resistance to deformation of the wall for those portions of the shell body 132 covered by the reinforcement members 134. Such reinforced wall portions of the shell body 134 will therefore tend to impart a greater force to a tooth biased against the interior surface of the reinforced part of the shell body 134 relative to unreinforced parts.

Figure 4:
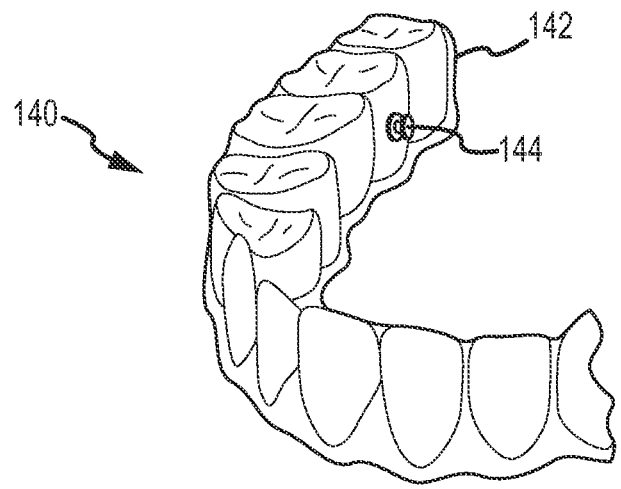
FIG. 4 shows a partial perspective view of a dental appliance with an auxiliary dental device in the form of a button bonded to a shell body.

Referring now to FIG. 4, a dental appliance 140 is shown including a shell body 142 and an auxiliary dental device, in the form of a button 144 for illustration. The button 144 is bonded to the lingual side of the shell body 142 by a cured product from curing a light-curable acrylic adhesive, according to the invention, disposed between a mounting surface of the button 144 and the adjacent exterior surface of the shell body 142. The button 144 may be of a metallic of polymeric material of construction, and may provide an attachment site, for example, for a rubber band or other feature used in an orthodontic treatment.

Figure 5:
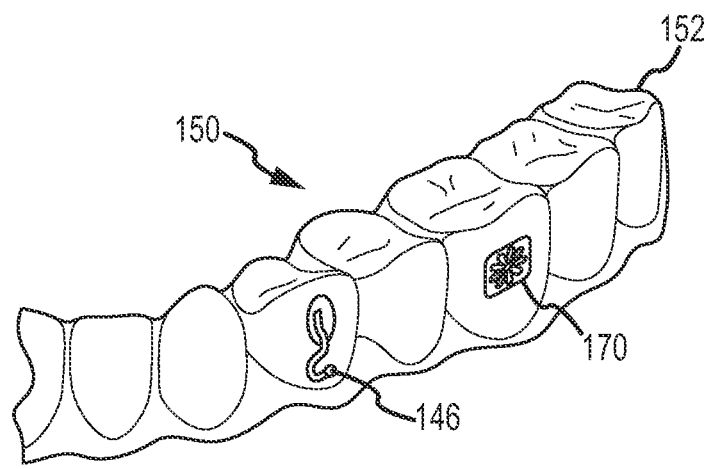
FIG. 5 shows a partial perspective view of a dental appliance with an auxiliary dental device in the form of a hook bonded to a shell body and a decal bonded to the shell body.

Referring now to FIG. 5, a dental appliance 150 is shown having a shell body 152 and an auxiliary dental device, in the form of a hook 146 for illustration. The hook 146 is bonded to an exterior surface of the shell body 152 on the facial side of the shell body 152. A mounting surface of the hook 146 is bonded to the shell body 152 through a cured product from curing a light-curable acrylic adhesive, according to the invention. FIG. 5 also shows a decorative decal 170 bonded to an exterior surface on the facial side of the shell body 152 through a cured product from curing a light-curable acrylic adhesive.

Figure 6:
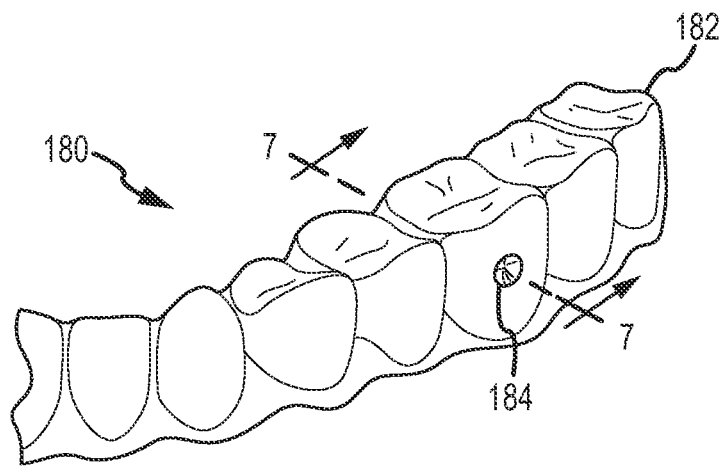
FIG. 6 shows a partial perspective view of a dental appliance with a reinforcing volume of cured product of a light-curable acrylic adhesive that reinforces a dimpled portion of a wall of a shell body.
Figure 7:
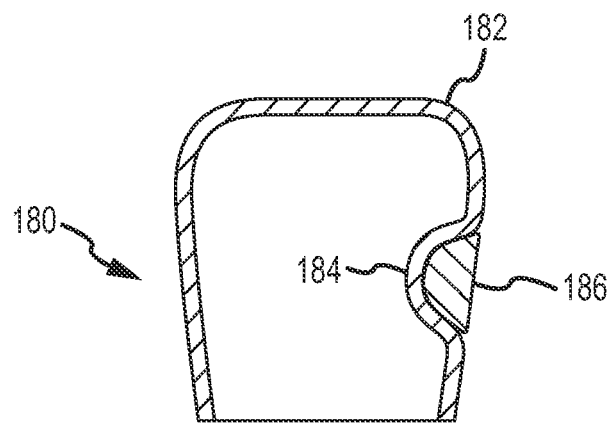
FIG. 7 shows a cross section of the dental appliance of FIG. 6 taken through a dimple with a recess filled with the cured product of the light-curable acrylic adhesive.

Referring now to FIGS. 6 and 7, a dental appliance 180 is shown having a shell body 182. The shell body 182 has a relief feature in the form of a dimple 184 having a recess on an exterior surface of the shell body and a corresponding protrusion on an interior surface of the shell body 182 in the compartment that receives teeth. As shown in FIG. 7, disposed in the recess of the dimple 184 and bonded to the exterior surface of the shell body 180 is a reinforcing volume 186 of cured product of light-curable acrylic adhesive. This has the effect of locally increasing the wall thickness of the dental appliance 180 in the vicinity of the dimple 184 to locally reinforce the wall, to apply a larger force to a tooth that may be positioned in contact with the protrusion of the dimple 184. The dimple 184 is shown on the facial side of the shell body, but could alternatively be located on the lingual side. A dental appliance may comprise multiple dimples or other wall relief features reinforced with reinforcing volumes of cured product of light-curable acrylic adhesive.

Many light-curable acrylic adhesive compositions for use with the invention are provided by or may include commercially-available adhesive products, including from Henkel under the LOCTITE® brand and from Dymax.

Examples of some possible light-curable adhesive products from Henkel include, as classified by Henkel:
Medical Grade, Acrylic Light Cured by Visible (w/Fluorescence):
LOCTITE® 3554™ Indigo™—bonds polycarbonate, thermoplastic, polyvinyl chloride
LOCTITE® 3555™ Indigo™—bonds polycarbonate, thermoplastic, polyvinyl chloride
LOCTITE® 3556™ Indigo™—bonds polycarbonate, thermoplastic, polyvinyl chloride
Medical Grade, Acrylic Light Cured by UV/Visible (w/Fluorescence):
LOCTITE® 3341™—bonds thermoplastics, polyvinylchloride
LOCTITE® 3911™—bonds glass, metal, thermoplastic
LOCTITE® 3921™—bonds glass, metal, thermoplastic, polycarbonate, polyvinylchloride
LOCTITE® 3922™—bonds glass, metal, thermoplastic, polycarbonate, polyvinylchloride
LOCTITE® 3924™—bonds glass, metal, thermoplastic, polycarbonate, polyvinylchloride
LOCTITE® 3926™—bonds glass, metal, thermoplastic, polycarbonate, polyvinylchloride
LOCTITE® 3933™—bonds glass, metal, thermoplastic, polycarbonate
LOCTITE® 3936™—bonds glass, metal, thermoplastic, polycarbonate
LOCTITE® 3941™—bonds glass, metal, thermoplastic, thermoset plastic
LOCTITE® 3942™—bonds glass, metal, thermoplastic, thermoset plastic
LOCTITE® 3943™—bonds glass, metal, thermoplastic, thermoset plastic
LOCTITE® 3944™—bonds glass, metal, thermoplastic, polycarbonate, polyvinylchloride
LOCTITE® 3971™—bonds metal, thermoplastic, polyvinylchloride, polyurethane
LOCTITE® 3972™—bonds metal, thermoplastic, polyvinylchloride, polyurethane
LOCTITE® 3974™—bonds thermoplastic, thermoset plastic, glass, metal, ceramic
Medical Grade, Acrylic Light Cured UV/Visible (w/o Fluorescence):
LOCTITE® 3201™—bonds glass, metal, thermoplastic, polycarbonate
LOCTITE® 3211™—bonds glass, metal, thermoplastic, polycarbonate
LOCTITE® 3301™—bonds glass, metal, thermoplastic, polycarbonate, polyvinylchloride
LOCTITE® 3311™—bonds glass, metal, thermoplastic, polycarbonate, polyvinylchloride
LOCTITE® 3321™—bonds glass, metal, thermoplastic, polycarbonate, polyvinylchloride
Medical Grade, Silicon Adhesives/Sealants Cured UV/Visible:
LOCTITE® 5240™ NUVA-SIL—bonds silicone, metal, glass, plastic
LOCTITE® 5055™—bonds silicone, metal, glass plastic
LOCTITE® 5056™—bonds silicone, metal, glass, plastic Examples of some possible useful light-curable adhesives products from Dymax include, as classified by Dymax:
Catheter and Guidewire-Bonding Adhesives:
203A-CTH-F™
204-CTH-F™
209-CTH™
Needle-Bonding and Syringe-Assembly Adhesives:
1161-M™
1162-M™
1180-M™
Respiratory-Device Adhesives: Anesthesia Masks, Resuscitator Bags, and Breathing Circuits:
109-MSK-UR™
110-MSK™
111-MSK™
MD Multipurpose Bonding Adhesives:
1128A-M™
1161-M™
1165-M™
1180-M™
1187-M™
1162-M™
MD Multipurpose Bonding Adhesives:
1128A-M™
1161-M™
1162-M™
1165-M™
1180-M™
1187-M™
See-Cure Adhesives:
1201-M-SC™

1202-M-SC™
1204-M-SC™

When the light-curable acrylic adhesive is to be formulated to prepare a colored layer, one or more pigment components may be added to provide the desired coloration to the cured layer. Examples of some commercially available pigment products include:

From Sun Chemical Performance Pigments: Suncroma™ Yellow Iron Oxide; Suncroma™ Red Iron Oxide; Suncroma™ Black Iron Oxide; Suncroma™ Tan Iron Oxide; Soft-Tex™ Yellow Iron Oxide; and Soft-Tex™ TiO2 White.

From Plasticolors: Chromacure™ TMPTA White; Chromacure™ TMPTA Black; and Chromacure™ TMPTA HS Phthalo Green.

From Ferro-Liquid Coatings and Dispersions Division: Black; Titanium Dioxide White; and Phthalo Blue.

The pigment within a light-curable acrylic adhesive composition according to the invention may include any one or more pigment components to provide desired coloration to the final cured product. For example, a mixture of pigment components will often be prepared when it is desired to match a tooth color. Table 1 shows information from Sun Chemical Performance Pigments on recommended mixtures of pigments for different tooth colors from the Vita Shade Guide.

TABLE 1

Sun Chemical Performance Pigments composition weight percents for different tooth colors from the Vita Shade Guide

|  | A0.5 | A1 | A2 | A3 | A3.5 | B1 | C1 | C2 | C3 | D2 | D3 |
|---|---|---|---|---|---|---|---|---|---|---|---|
| Suncroma Red Iron Oxide |  |  |  |  |  | 0.17 |  |  |  | 0.27 | 0.40 |
| Suncroma Black Iron Oxide | 0.22 | 0.45 | 0.97 | 0.96 | 0.87 | 0.58 | 2.22 | 1.86 | 2.69 | 0.69 | 1.05 |
| Suncroma Yellow Iron Oxide |  |  |  |  |  | 4.45 |  | 0.21 |  |  |  |
| Soft-Tex Yellow Iron Oxide | 1.15 | 2.30 | 5.00 | 6.71 | 14.73 |  | 2.95 | 5.44 | 3.95 | 1.70 | 2.20 |
| Suncroma Tan Iron Oxide | 1.12 | 2.25 | 4.88 | 4.79 | 4.38 |  | 1.98 | 2.29 | 4.64 | 2.66 | 3.59 |
| Soft-Tex TiO2 White | 97.50 | 95.00 | 89.15 | 87.54 | 80.01 | 94.80 | 92.85 | 90.20 | 88.72 | 94.68 | 92.75 |

When used in the light-curable acrylic adhesive, a fragrance may include any one or more fragrance components to impart a desired scent to the final cured product. Examples of some fragrances available from Bell Flavors & Fragrances include: 6109090 Mint Fragrance; 6110924 Mint Fragrance; 6113676 Green Herbal Fragrance; and 6112109 Green Fruity Herbal Fragrance.

EXAMPLES

Example 1

LOCTITE® 3554™ Indigo™, LOCTITE® 3556™ Indigo™, LOCTITE® 3971™ and LOCTITE® 3972™ are some preferred commercially available adhesives for use as or to make the light-curable acrylic adhesive used with the invention. These are all medical grade adhesive products, with LOCTITE® 3554™ Indigo™ and LOCTITE® 3556™ Indigo™ products being light-curable with visible light and the LOCTITE® 3971™ and LOCTITE® 33972™ products being light-curable with UV/visible light. Compositional information for these adhesive products are summarized in Tables 2-5 using component listing, CAS number and weight percentage information as provided on Material Data Safety Sheets, and showing the material type for those components as estimated by the inventors. Each of these adhesives is tested qualitatively for adhesion to a polyvinyl chloride test substrate. The adhesives are cured using a standard dental light. All of the cured adhesives show good adhesion to the substrate.

TABLE 2

LOCTITE ® 3554 ™ Indigo ™*

| Component | CAS Number | Weight % | Material Type |
|---|---|---|---|
| aliphatic urethane acrylate oligomer | unknown | 10-30 | acrylate base material |
| urethane acrylate oligomer | proprietary | 10-30 | acrylate base material |
| hexafunctional urethane acrylate ester | unknown | 5-10 | acrylate base material |
| modified acrylamide | 2680-03-7 | 10-30 | unsaturated adhesion promoter |
| diacrylate ester | proprietary | 10-30 | unsaturated adhesion promoter |

TABLE 2-continued

LOCTITE ® 3554 ™ Indigo ™*

| Component | CAS Number | Weight % | Material Type |
|---|---|---|---|
| acrylic ester | unknown | 5-10 | unsaturated adhesion promoter |
| methacrylate ester | proprietary | 1-5 | unsaturated adhesion promoter |
| Photoinitiator | proprietary | 1-5 | Photoinitiator |

*Component listing, CAS Number and weight percent from supplier's Material Data Safety Sheet dated Jul. 30, 2007

TABLE 3

LOCTITE ® 3556 ™ Indigo ™*

| Component | CAS Number | Weight % | Material Type |
|---|---|---|---|
| aliphatic urethane acrylate oligomer | unknown | 30-60 | acrylate base material |

TABLE 3-continued

LOCTITE ® 3556 ™ Indigo ™*

| Component | CAS Number | Weight % | Material Type |
|---|---|---|---|
| modified acrylamide | 2680-03-7 | 10-30 | unsaturated adhesion promoter |
| acrylic ester | unknown | 10-30 | unsaturated adhesion promoter |
| methacrylate ester | proprietary | 1-5 | unsaturated adhesion promoter |
| diacrylate ester | 13048-33-4 | 1-5 | unsaturated adhesion promoter |
| Photoinitiator | proprietary | 1-5 | Photoinitiator |
| APEx-T Resin | unknown | 10-30 | Unidentified |
| Silica, amorphous, fumed, crystalline-free | 112945-52-5 | 1-5 | Other |

*Components, CAS Number and weight percent information from supplier's Material Data Safety Sheet dated Aug. 1, 2007

TABLE 4

LOCTITE ® 3971 ™*

| Component | CAS Number | Weight % | Material Type |
|---|---|---|---|
| urethane acrylate oligomer | unknown | 10-30 | acrylate base material |
| urethane acrylate | unknown | 5-10 | acrylate base material |
| modified acrylamide | 2680-03-7 | 10-30 | unsaturated adhesion promoter |
| acrylate ester | 2399-48-6 | 5-10 | unsaturated adhesion promoter |
| acrylate ester | 7328-17-8 | 1-5 | unsaturated adhesion promoter |
| acrylic acid | 79-10-7 | 1-5 | unsaturated adhesion promoter |
| diacrylate ester | 42978-66-5 | 1-5 | unsaturated adhesion promoter |
| photoinitiator | proprietary | 1-5 | Photoinitiator |
| photoinitiator | 947-19-3 | 1-5 | Photoinitiator |
| isobornyl acrylate | 5888-33-5 | 10-30 | Other |
| gamma-glycidoxypropyl trimethoxysilane | 2530-83-8 | 1-5 | Other |

*Component listing, CAS Number and weight percent from supplier's Material Data Safety Sheet dated Mar. 17, 2009

TABLE 5

LOCTITE ® 3972 ™*

| Component | CAS Number | Weight % | Material Type |
|---|---|---|---|
| urethane acrylate oligomer | unknown | 30-60 | acrylate base material |
| urethane acrylate prepolymer | proprietary | 5-10 | acrylate base material |
| modified acrylamide | 2680-03-7 | 10-30 | unsaturated adhesion promoter |
| acrylate monomer | proprietary | 10-30 | unsaturated adhesion promoter |
| diacrylate ester | proprietary | 5-10 | unsaturated adhesion promoter |
| acrylate ester | proprietary | 1-5 | unsaturated adhesion promoter |
| acrylic acid | 79-10-7 | 1-5 | unsaturated adhesion promoter |
| photoinitiator | proprietary | 1-5 | Photoinitiator |
| photoinitiator | proprietary | 1-5 | Photoinitiator |
| gamma-glycidoxypropyl trimethoxysilane | 2530-83-8 | 1-5 | Other |
| hydroquinone | 123-31-9 | 0.1-1 | Other |

*Component listing, CAS Number and weight percent from supplier's Material Data Safety Sheet dated Mar. 14, 2009

Example 2

Dymax 1187-M™ is another particular commercial adhesive product identified for use as or to prepare the light-curable acrylic adhesive according to the invention. Compositional information for this adhesive product is summarized in Table 6, with component listing and weight percentage information as reported on a Material Safety Data Sheet, and showing the material type for those components as estimated by the inventors. The adhesive product also includes photoinitiator, not shown.

TABLE 6

1187-M ™*

| Component | CAS Number | Weight % | Material Type |
|---|---|---|---|
| urethane acrylate oligomer | | 25-50 | acrylate base material |
| N,N-dimethylacrylamide | 2680-03-7 | 15-25 | unsaturated adhesion promoter |
| isobornyl acrylate | 5888-33-5 | 25-50 | Other |
| epoxy resin | | <1 | Other |

*Component listing, CAS Number and weight percent from supplier's Material Data Safety Sheet dated Jun. 29, 2009.

Example 3

Two example formulations are made for a light-curable acrylic adhesive by mixing commercially-available adhesive products. One formulation is a 50:50 (weight) mixture of LOCTITE® 3971™ and LOCTITE® 3972™. The other formulation is a 50:50 (weight) mixture of LOCTITE®3554™ Indigo™ and LOCTITE®3556™ Indigo™. The formulations are tested qualitatively for adhesion to a polyvinyl chloride test substrate. The formulations are cured using a standard dental light. Both cured formulations show good adhesion to the substrate.

Example 4

Three example formulations are made for a light-curable acrylic adhesive containing pigment and useful as "paint formulations" for preparation of a colored layer on a shell body of a dental appliance. The three example formulations (Formulations A, B, C) are summarized in Table 7.

TABLE 7

| Component | Formulation A Weight % | Formulation B Weight % | Formulation C Weight % |
|---|---|---|---|
| LOCTITE ® 3971 ™ | 48.5 | 47.5 | |
| LOCTITE ® 3972 ™ | 48.5 | 47.5 | |
| LOCTITE ® 3554 ™ INDIGO ™ | | | 47.5 |
| LOCTITE ® 3556 ™ INDIGO ™ | | | 47.5 |
| A2 Pigment Blend* | 3 | 3 | 5 |
| Mint Fragrance** | | 2 | |

*A2 Vita Shade Guide pigment blend with Sun Chemical Performance Pigment pigment products per Table 1
**Bell Flavors & Fragrances 6109090 Mint Fragrance Formulations A, B and C are tested for adhesion to a polyvinyl chloride test substrate, cured using a standard dental light. All cured formulations show good adhesion to the substrate.

Example 5

Five Example formulations are prepared containing pentaerythritol tetra-3-mercaptopropionate (PETMP) as a thiol monomer. The example formulations (Formulations D-H) are summarized in Table 8.

TABLE 8

| Component | Formulation D Weight % | Formulation E Weight % | Formulation F Weight % | Formulation G Weight % | Formulation H Weight % |
|---|---|---|---|---|---|
| LOCTITE ® 3971 ™ | | 47.5 | 45.5 | | |
| LOCTITE ® 3972 ™ | | 47.5 | 45.5 | | |
| LOCTITE ® 3454 ™ INDIGO ™ | | | | 47.5 | 45.5 |
| LOCTITE ® 3555 ™ INDIGO ™ | 85.81 | | | | |
| LOCTITE ® 3556 ™ INDIGO ™ | | | | 47.5 | 45.5 |
| PETMP | 8.75 | 5 | 9 | 5 | 9 |
| Iron Oxide Pigments* | 0.15 | | | | |
| TiO$_2$ Pigment | 3.35 | | | | |
| Mint Fragrance | 1.94 | | | | |

*black, yellow and tan

The formulations are tested qualitatively for adhesion to a polyvinyl chloride test substrate. The formulations are cured using a standard dental light. All cured formulations show good adhesion to the substrate and good strength and toughness, tested through probing the cured product by hand with a metal hook of a type used by dentists to probe teeth.

Example 6

Light-curable adhesive formulations are prepared including LOCTITE® 3454™ INDIGO™, LOCTITE® 3555™ INDIGO™, LOCTITE® 3971™ and LOCTITE® 3972™ with added PETMP (pentaerythritol tetra(3-mercaptopropionate)) as a thiol monomer in amounts of about 5 to 25 weight percent relative to the respective LOCTITE® composition. The formulations are curable to form a cured adhesive with good adhesion. However, the shelf-life of these adhesive formulations is very short, and if used such formulations should be mixed on site immediately prior to use. It is believed that the short shelf-life is due to stability issues between the thiol monomer and modified acrylamide or similar components of LOCTITE® compositions.

Light-curable adhesive formulations are prepared from ingredients shown in Table 9. The compositions of specific adhesive formulations (Formulations I-N) are shown in Table 10. Formula I is one preferred non-pigmented adhesive composition, such as for bonding auxiliary dental devices to polymeric shell bodies of dental appliances, and Formula J is one preferred pigmented adhesive composition, such as for forming a colored layer on polymeric shell bodies of dental appliances.

TABLE 9

| Ingredient | Source | Chemical Component | Component Material Type |
|---|---|---|---|
| CN9783 | Sartomer USA, LLC | aromatic urethane acrylate | acrylate base material |
| SR606A | Sartomer USA, LLC | polyester diacrylate | acrylate base material or unsaturated adhesion promoter |
| SB520E35 | Sartomer USA, LLC | ethoxylated (3) trimethylolpropane triacrylate (in composition with aromatic acid acrylate half ester) | acrylate base material |
| SR833S | Sartomer USA, LLC | tricyclodecane dimethanol diacrylate | acrylate base material or unsaturated adhesion promoter |
| SR213 | Sartomer USA, LLC | 1,4-butadediol diacrylate | unsaturated adhesion promoter |
| SR339 | Sartomer USA, LLC | 2-phenoxyethyl acrylate | unsaturated adhesion promoter |
| SR349 | Sartomer USA, LLC | ethoxylated (3) bisphenol A diacrylate | unsaturated adhesion promoter |
| dimethylacrylamide | | Dimethylacrylamide | unsaturated adhesion promoter |
| PETMP | | pentaerythritol tetra(3-mercaptopropionate) | thiol monomer |
| Irgacure 819 | BASF/Ciba Specialty Chemicals | | photoinitiator |
| NPAL | Albemarle Corporation | aluminum N-nitrosophenylhydroxylamine | other (radical inhibitor) |
| BHT | | Butylhydroxytoluene | other |
| fumed silica | | | other |
| mint oil | | | fragrance |
| yellow iron oxide pigment | | | pigment |

TABLE 10

| Component | Formulation I Weight % | Formulation J Weight % | Formulation K Weight % | Formulation L Weight % | Formulation M Weight % | Formulation N Weight % |
|---|---|---|---|---|---|---|
| CN9783 | 49.5 | | 50 | | 49.5 | |
| SR606A | | | 39.1 | 59.1 | | |
| SB520E35 | | | | | | 64.5 |
| SR833S | 20 | 50 | | | | |
| SR213 | 20 | 36.5 | | | | |
| SR339 | | | | 30 | | 25 |
| SR349 | | | | | 20 | |
| Dimethyl-acrylamide | | | | | 20 | |
| PETMP | 10 | 10 | 10 | 10 | 10 | 10 |
| Irgacure 819 | 0.4 | 0.4 | 0.6 | 0.6 | 0.4 | 0.4 |
| NPAL | 0.1 | 0.2 | | | 0.1 | 0.1 |
| BHT | | | 0.3 | 0.3 | | |
| fumed silica | | 2 | | | | |
| mint oil | | 0.4 | | | | |
| yellow iron oxide pigment | | 0.5 | | | | |

Formulations I and J show good stability over a three-month period. Both formulations are curable to form a cured adhesive with good adhesion. Formulation I after curing shows good adhesion to polyethylene terephthalate substrates, with and without prior pretreatment of the surface the substrate with. For many other polymeric substrates, good adhesion for Formulation I is obtained when the substrate is subjected to a prior surface pretreatment with an adhesion promoter.

Formulation J is a pigmented adhesive formulation, and after curing shows good adhesion to a number of polymeric substrates when the substrate has been subjected to prior surface pretreatment with an adhesion promoter.

Formulation K after curing shows good adhesion to a number of polymeric substrates when the substrate has been subjected to a prior surface pretreatment with an adhesion promoter.

Formulation L after curing shows higher shrinkage than other formulations shown in Table 10, but also shows good adhesion to a number of polymeric substrates when the substrate has been subjected to a prior surface pretreatment with an adhesion promoter.

Formulation M after curing shows good adhesion to many polymeric substrates even without prior surface pretreatment with an adhesion promoter. With the use of a prior surface pretreatment with an adhesion promoter, Formulation M after curing shows good adhesion on additional polymeric substrates. However, after soaking overnight in water at 50° C., the cured product of Formulation M failed, which may be due to the hydrophobic nature of dimethylacrylamide in the adhesive formulation allowing water to plasticize the composition and cause a loss in strength.

Formulation N after curing shows very good adhesion to a number of polymeric substrates when the substrate has been subjected to a prior surface pretreatment with an adhesion promoter.

Example 7

The Formulation I adhesive of Example 6 is tested against ClearLoc™ adhesive (Align Technology, Inc.) using a Mini Bionix® II Test System available from MTS Systems Corporation to evaluate relative adhesive performance. The test samples used in this test include metal buttons adhered to polymeric aligner material made from polyvinyl chloride supplied by Great Lakes Biocryl. For the ClearLoc™ samples, no pretreatment or priming of the aligner material is used per the advertised instructions for the product. The ClearLoc™ adhesive is applied to the button and the button is placed on top of the adhesive on the aligner material. The ClearLoc™ adhesive is cured for 30 seconds with a 3M dental curing light. A total of twenty samples using the ClearLoc™ adhesive are prepared in this manner. For the Formulation I samples, the aligner material is primed (surface pretreated) by application of N-vinylpyrrolidone a cotton tipped applicator to the surface portion of the aligner material to which the metal button is to be bonded. The Formulation I adhesive is applied to the button and the button was placed on the pretreated (primed) surface of the aligner. The Formulation I adhesive is cured for 30 seconds with a 3M dental curing light. A total of twenty-one samples using Formulation I adhesive are prepared in this manner.

Each sample is soaked in room temperature water for 30 minutes before performing an adhesion test on the sample. Water soaking has been found to cause loss of adhesion in certain materials. The adhesion test included a custom made "chisel" disposed at the interface of the button and adhesive. With a head speed of 1 mm/min, the chisel was used to apply a load to the interface of the button and adhesive. The maximum force recorded by the Mini Bionix® II Test System prior to failure is shown in Table 11 for the ClearLoc™ samples and the Formulation I adhesive samples.

TABLE 11

| | Maximum Force (in Newtons) | |
|---|---|---|
| Sample | ClearLoc ™ | Formulation I |
| 1 | 33.3 | 32.5 |
| 2 | 23.65 | 170.9 |
| 3 | 33.7 | 100.6 |
| 4 | 30.2 | 122.4 |
| 5 | 22.6 | 86.5 |
| 6 | 37.5 | 146 |
| 7 | 28.7 | 170.9 |
| 8 | 15.8 | 126.8 |
| 9 | 37.7 | 96.9 |
| 10 | 40.8 | 119.3 |
| 11 | 28.8 | 68.4 |
| 12 | 20.1 | 104.7 |
| 13 | 25.7 | 84.2 |
| 14 | 16.1 | 63.4 |
| 15 | 20.9 | 138.6 |
| 16 | 34.6 | 143.6 |

TABLE 11-continued

| | Maximum Force (in Newtons) | |
|---|---|---|
| Sample | ClearLoc ™ | Formulation I |
| 17 | 22.5 | 95.1 |
| 18 | 35.1 | 123.1 |
| 19 | 24.2 | 148.4 |
| 20 | 33.7 | 85.5 |
| 21 | | 103 |
| Average | 28 | 111 |
| Standard Deviation | 7 | 35 |

As seen from Table 11, Formulation I demonstrates significantly better adhesion performance as evidenced by the substantially increased maximum force experienced prior to failure. All ClearLoc™ samples failed at the interface of the adhesive and aligner material. A majority of the Formulation I samples experienced yielding of the aligner material rather than adhesive failure.

The foregoing discussion of the invention has been presented for purposes of illustration and description and to disclose the best mode contemplated for practicing the invention. The foregoing is not intended to limit the invention to only the form or forms specifically disclosed herein. Although the description of the invention has included description of one or more embodiments and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described with respect to any disclosed embodiment, implementation, variation or configuration may be combined in any combination with one or more features of any other embodiment, implementation, variation or configuration.

The terms "comprising", "containing", "including" and "having", and variations thereof, are intended to be inclusive and nonlimiting in that the use of such terms indicates the presence of some condition or feature, but not to the exclusion of the presence also of any other condition or feature. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

What is claimed is:

1. A dental appliance positionable to be worn within the oral cavity to receive and cover at least a portion of a dentition of a subject, comprising:
    a shell body comprised of polymeric material, the shell body comprising an interior surface of a compartment within the shell body configured to receive at least a portion of one or more tooth of the dentition when the appliance is worn, the shell body comprising an exterior surface opposite the interior surface; and
    an auxiliary feature bonded to the polymeric material of the shell body with a cured product of a light-curable acrylic adhesive, the light-curable acrylic adhesive comprising:
        acrylate base material comprising multiple polymerizable acrylic functionality;
        thiol monomer copolymerizable with the acrylate base material; and
        photoinitiator.

2. A dental appliance according to claim 1, wherein the cured product comprises a fragrance that imparts an odor to the cured product.

3. A dental appliance according to claim 1, wherein the auxiliary feature comprises an auxiliary dental device bonded to at least a portion of the external surface of the shell body.

4. A dental appliance according to claim 3, wherein the auxiliary dental device comprises a metallic surface bonded to the polymeric material of the shell body through the cured product.

5. A dental appliance according to claim 3, wherein the auxiliary dental device comprises a polymeric surface that is bonded to the polymeric material of the shell body through the cured product.

6. A dental appliance according to claim 1, wherein the polymeric material comprises a member selected from the group consisting of ethylene vinyl acetate, polycarbonate, low-density polyethylene, polypropylene, polyethylene terephthalate, polybutyrate, sheet acrylic and polyvinyl chloride.

7. A dental appliance according to claim 1, wherein the light-curable acrylic adhesive comprises an unsaturated adhesion promoter copolymerizable with the acrylic functionalities of the acrylate base material.

8. A dental appliance according to claim 7, wherein the unsaturated adhesion promoter comprises at least one adhesion-promoting moiety comprising a carbonyl group.

9. A dental appliance according to claim 8, wherein the adhesion-promoting moiety is an amide group.

10. A dental appliance according to claim 8, wherein the amide compound is dimethylacrylamide.

11. A dental appliance according to claim 7, wherein the light-curable acrylic adhesive comprises from 15 weight percent to 80 weight percent of the unsaturated adhesion promoter.

12. A dental appliance according to claim 1, wherein the acrylate base material comprises at least two acrylate groups.

13. A dental appliance according to claim 1, wherein the acrylate base material comprises tricyclodecane dimethanol diacrylate.

14. A dental appliance according to claim 1, wherein the light-curable acrylic adhesive comprises from 10 weight percent to 70 weight percent of the acrylate base material.

15. A dental appliance according to claim 1, wherein the thiol monomer comprises at least one polythiol compound.

16. A dental appliance according to claim 1, comprising from 2 weight percent to 40 weight percent of the thiol monomer.

17. A dental appliance according to claim 16, wherein the thiol monomer comprises pentaerythritol tetra(3-mercaptopropionate).

18. A dental appliance according to claim 1, wherein the light-curable acrylic adhesive comprises an unsaturated adhesion promoter copolymerizable with the acrylic functionality of the acrylate base material and with the thiol monomer.

19. A dental appliance according to claim 1, wherein;
    the acrylate base material comprises tricyclodecane dimethanol diacrylate;

the light-curable acrylic adhesive comprises an unsaturated adhesion promoter copolymerizable with the acrylic functionalities of the acrylate base material, the unsaturated adhesion promoter comprising dimethylacrylamide;

the thiol monomer comprises pentaerythritol tetra(3-mercaptopropionate); and the light curable acrylic adhesive comprises:
- from 20 weight percent to 70 weight percent of the acrylate base material;
- from 15 weight percent to 60 weight percent of the unsaturated adhesion promoter;
- from 2 weight percent to 25 weight percent of the thiol monomer; and
- a combined concentration of the acrylate base material and the unsaturated adhesion promoter in a range of from 60 weight percent to 95 weight percent.

20. A method of orthodontic treatment for repositioning one or more tooth of a patient, the method comprising positioning a dental appliance according to claim 1 within the oral cavity of the patient to cover at least a portion of the dentition of the patient with one or more tooth received within the compartment and biased by the stricture of the shell body to cause movement of the one or more tooth.

21. A dental appliance positionable to be worn within the oral cavity to receive and cover at least a portion of a dentition of a subject, comprising:
- a shell body comprised of polymeric material, the shell body comprising an interior surface of a compartment within the shell body configured to receive at least a portion of one or more tooth of the dentition when the appliance is worn, the shell body comprising an exterior surface opposite the interior surface; and
- an auxiliary feature bonded to the polymeric material of the shell body with a cured product of a light-curable acrylic adhesive, the light-curable acrylic adhesive comprising: acrylate base material comprising multiple polymerizable acrylic functionality; and photoinitiator;
- wherein the shell body has a facial side disposed on a facial side of the dentition when the appliance is worn and the shell body has a lingual side disposed on a lingual side of the dentition when the appliance is worn; and
- wherein the auxiliary feature comprises coloration provided by a colored layer of the cured product covering at least a portion of one or both of the interior surface and exterior surface of the shell body, the cured product comprising a pigment that imparts the coloration to the cured product; and
- wherein the colored layer of the cured product imparts coloration to at least a portion of the facial side of the shell body and is visible when the shell body is viewed from the facial side to provide decorative appearance over a corresponding portion of the compartment, said corresponding portion of the compartment being disposed toward the lingual side of the shell body relative to the colored layer of the cured product and being open to receive one or more tooth of the dentition.

22. A dental appliance according to claim 21, wherein the light-curable acrylic adhesive comprises from 0.1 weight percent to 10 weight percent of the pigment.

23. A dental appliance according to claim 22, where in the colored layer of the cured product is bonded to and covers at least a portion of the interior surface located on the facial side of the shell body; and the shell body is transparent at least through the facial side of the shell body adjacent the colored layer of the cured product.

24. A method of orthodontic treatment for repositioning one or more tooth of a patient, the method comprising positioning a dental appliance according to claim 21 within the oral cavity of the patient to cover at least a portion of the dentition of the patient with one or more tooth received within the corresponding portion of the compartment and with at least one tooth biased by the structure of the shell body to cause movement of the at least one tooth.

25. A dental appliance positionable to be worn within the oral cavity to receive and cover at least a portion of a dentition of a subject, comprising:
- a shell body comprised of polymeric material, the shell body comprising an interior surface of a compartment within the shell body configured to receive at least a portion of one or more tooth of the dentition when the appliance is worn, the shell body comprising an exterior surface opposite the interior surface; and
- an auxiliary feature bonded to the polymeric material of the shell body with a cured product of a light-curable acrylic adhesive, the light-curable acrylic adhesive comprising: acrylate base material comprising multiple polymerizable acrylic functionality; and photoinitiator;
- wherein the auxiliary feature comprises coloration provided by a colored layer of the cured product covering at least a portion of one or both of the interior surface and exterior surface of the shell body, the cured product comprising a pigment that imparts the coloration to the cured product;
- wherein the light-curable acrylic adhesive comprises from 0.1 weight percent to 10 weight percent of the pigment;
- wherein the shell body has an occlusal side that covers at least a portion of the biting surfaces of the dentition when the appliance is worn; and
- wherein the colored layer of the cured product imparts coloration to at least a portion of the occlusal side of the shell body when the appliance is worn.

26. A method of orthodontic treatment for repositioning one or more tooth of a patient, the method comprising positioning a dental appliance according to claim 25 within the oral cavity of the patient to cover at least a portion of the dentition of the patient with one or more tooth received within the compartment and biased by the structure of the shell body to cause movement of the one or more tooth.

27. A dental appliance according to claim 25, wherein the colored layer of the cured product provides decorative appearance from the occlusal side over a corresponding portion of the compartment open to receive one or more tooth of the dentition.

28. A method for making a dental appliance positionable to be worn within the oral cavity to receive and cover at least a portion of a dentition of a subject:
- applying a light-curable acrylic adhesive to a surface of polymeric material of a shell body comprising an interior compartment to receive at least a portion of one or more tooth of the dentition when the appliance is worn;
- in the absence of having any portion of a tooth received in the interior compartment, curing the light-curable acrylic adhesive, the curing comprising after the applying subjecting the light-curable acrylic adhesive to a light source sufficient to cause the light-curable acrylic adhesive to cure to form a cured product bonded to the surface of the polymer material;

the light-curable acrylic adhesive comprising:
- acrylate base material comprising multiple polymerizable acrylic functionality;
- thiol monomer copolymerizable with the acrylate base material; and
- photoinitiator.

29. A method according to claim 28, wherein:
- the shell body has a facial side disposed on a facial side of the dentition when the appliance is worn and the shell body has a lingual side disposed on a lingual side of the dentition when the appliance is worn; and
- the light-curable acrylic adhesive comprises a pigment that imparts to the cured product coloration that is visible when the shell body is viewed from the facial side of the shell body.

30. A method according to claim 28, comprising during the curing, bonding an auxiliary dental device to the surface of the polymeric material with the cured product of the light-curable acrylic adhesive.

31. A method according to claim 28, comprising prior to the applying, pretreating the surface, the pretreating comprising contacting the surface with a pretreatment composition that alters the surface.

32. A method according to claim 28, wherein the light-curable acrylic adhesive comprises an unsaturated adhesion promoter copolymerizable with the acrylate base material.

* * * * *